(12) United States Patent
Dickinson et al.

(10) Patent No.: US 6,387,332 B1
(45) Date of Patent: May 14, 2002

(54) SAFETY SYSTEM

(75) Inventors: Warren P. Dickinson, Lansing; Franklin S. Lange, Buffalo Grove; James S. Legg, Palos Heights, all of IL (US)

(73) Assignee: Griffith Micro Science, Inc., Oak Brook, IL (US)

( * ) Notice: Subject to any disclaimer, the term of this patent is extended or adjusted under 35 U.S.C. 154(b) by 0 days.

(21) Appl. No.: 09/240,377

(22) Filed: Jan. 29, 1999

(51) Int. Cl.[7] .............................. A61L 2/00; G05B 9/00; G01V 3/00; E05F 15/20
(52) U.S. Cl. ............................. 422/117; 422/2; 422/26; 422/105; 422/292; 324/314; 324/316; 324/600; 49/29
(58) Field of Search .................. 422/1–3, 34, 62, 422/105, 117, 119, 292, 295, 26, 112, 113; 324/314, 316, 600–699; 49/29

(56) References Cited

U.S. PATENT DOCUMENTS

| | | | |
|---|---|---|---|
| 3,197,692 A | 7/1965 | Hyde | 324/0.5 |
| 3,348,136 A | 10/1967 | Nelson et al. | 324/0.5 |
| 3,350,633 A | 10/1967 | Hyde | 324/0.5 |
| 3,372,331 A | 3/1968 | Larson | 324/0.5 |
| 3,502,485 A | 3/1970 | Illouze | 99/154 |
| 3,585,494 A | 6/1971 | Bozanic et al. | 324/0.5 |
| 3,650,038 A * | 3/1972 | Alessi et al. | 34/45 |
| 3,676,058 A | 7/1972 | Gray | 21/54 R |
| 3,691,453 A | 9/1972 | Rupp, Jr. et al. | 324/0.5 R |
| 3,691,454 A | 9/1972 | Hubresh | 324/0.5 R |
| 4,207,286 A | 6/1980 | Gut Boucher | 422/21 |
| 4,239,731 A * | 12/1980 | Gillis et al. | 422/112 |
| 4,426,358 A * | 1/1984 | Johansson | 422/112 |
| 4,593,248 A | 6/1986 | Hyde et al. | 324/317 |
| 5,209,902 A | 5/1993 | Matthews | 422/21 |
| 5,399,314 A * | 3/1995 | Samuel et al. | 422/34 |
| 5,401,394 A * | 3/1995 | Markham | 210/85 |
| 5,520,893 A * | 5/1996 | Kasting, Jr. et al. | 422/305 |
| 5,548,217 A | 8/1996 | Gibson | 324/316 |

OTHER PUBLICATIONS

R. J. Collier, "Variable–Frequency Microwave Cavity Spectrometer", REview of Scientific Instrum., vol. 25, No. 12, Dec. 1954.

A. Dymanus, "High–Q Stark Cavity Absorption Cell for Microwave Spectrometers", Review of Scientific Instrum., vol. 30, No. 3, Mar. 1959.

L. W. Hrubesth et al. "A Gunn Diode Microwave Cavity Spectrometer", University of Wymoming, 1969.

L. W. Hrubest et al., "A Cavity Search Spectrometer for Free Radial Microwave Rotational Absorption Studies", Review of Scientific Instrum., vol. 42, No. 4, Jun. 1971.

(List continued on next page.)

Primary Examiner—Robert J. Warden, Sr.
Assistant Examiner—Monzer R. Chorbaji
(74) Attorney, Agent, or Firm—Dorsey & Whitney LLP

(57) ABSTRACT

A safety system for a gas process or facility for measuring the concentration of a specified gas in an area or chamber and determining whether it is safe to allow access to such area or chamber. In particular, the safety system is adapted for use in a gas sterilization facility having one or more sterilization chambers, wherein the safety system measures the concentration of the sterilizing gas and unlocks the door of the sterilization chamber if the level of the sterilizing gas in the sterilization chamber is below a predetermined limit. The safety system further limits access to the sterilization chamber after a predetermined period of time if the door of the sterilization chamber is not opened due to the possible continued desorption of the sterilizing gas from the articles into the sterilization chamber.

9 Claims, 4 Drawing Sheets

OTHER PUBLICATIONS

R. B. Roberts et al., "Aeration After Ethylene Oxide Sterilsation", Anaesthesia, vol. 27, No. 3, Jul. 1972.

H. Uehara et al., Continuous Ammonia Monitor Using a Stark Microwave Cavity Resonator Onator, Review of Scientific Instrum., vol. 51, No. 3, Mar. 1980.

W. F. Kolbe et al., "140 GHz Microwave Spectrometer for the Detection of Gaseous Chemical Species", University of California, Apr. 25, 1983.

A. H. Samuel, "Microwave Desportion: A Combined Sterilizer/Aerator for the Accelerated Elimination of Ethylene Oxide Residues from Sterilized Supplies", Medical Instrumentation, vol. 22, No. 1, 1988.

G. Gibson et al., "Microwave Enhanced Diffusion in Polymeric Materials", International Microwave Power Institute, vol. 23, No. 1, 1988.

G. Gibson et al., "Computerized Model for Accurate Determination of Ethylene Oxide Diffusion in Sterilized Medical Supplies", Biomaterials, vol. 10, Jul. 1989.

I.P. Matthews et al., "Enhancement of the Kinetics of the Aeration of Ethylene Oxide Sterilized Polymers Using Microwave Radiation", Journal of Biomedical Materials Research, vol. 23, 1989.

Z. Zhu, "Parametric Monitoring and Control of the Ethylene Oxide Sterilization Process—A Microwave Cavity Spectrometer for Process Monitoring of Gas Concentrations", Doctor of Philosophy, A Thesis, University of Wales, Apr. 1992.

Z. Zhu et al., "A Gas Monitoring System For Ethylene Oxide Sterilizers, With Constant Sample Flow Through a Microwave Cavity Spectrometer", Journal of Medical Engineering & Technology, vol. 17, No. 4, Jul./Aug. 1993.

Z. Zhu et al. "A Microwave Spetometer With a Frequency Control System Employing a Frequency 'Scanning Window' Locked to the Rotational Absorption Peak", Review of Scientific Instrum., vol. 6, No. 10, Oct. 1995.

Z. Zhu et al., Quantitative Measurement of Analyte Gases in a Microwave Spectrometer Using a Dynamic Sampling Method, Review of Scientific Instrum., vol. 67, No. 7, Jul. 1996.

P. J. Sordellini, "Speeding EtO–Sterilized Products to Market with Parametric Release", Medical Device & Diagnostic Industry, Feb. 1997.

Z. Zhu et al., "Specificity, Accuracy, and Interpretation of Measurements of Ehtylene Oxide Gas Concentration During Sterilization Using a Microwave Spectrometer", Review of Scientific Instrum., vol. 68, No. 7, Jul. 1997.

I. P. Matthews et al., "Parametric Release for EtO Sterilization", Medical/Device Technology, Jul./Aug. 1998.

G.E. Reesor et al., "X–band Spectrometer with a Rectangular Stark Cell", Dept. of Physics, University of Waterloo, Waterloo, Ontario, Canada, Feb. 27, 1975.

W. Fehse et al., "The Construction of a Microcompute Controlled Microwave–Microwave Double Resonance Spectrometer Incorporating Two Crossed Fabry–Perot Resonators", Journal of Molecular Structure, 97 (1983) 263–270.

W. F. Kolbe et al., "GHz Pulsed Fouerier transform Microwave Spectrometer", University of California, Sep. 26, 1984.

M. C. Lee et al., "A Cavity Type Absorption Cell for Double Resonance Microwave Spectroscopy", Review of Scientific Instrum., vol. 43, No. 4, Nov. 1971.

R. N. Nandi et al., "Microwave–Microwave Double Resonance Using a Fabry–Perot Cavity Spectrometer", University of Kansas, Jun. 1983.

H. Uehara et al., "A Sensitive Microwave Cavity Spectrometer: Direct Detection of Formaldehyde in Automobile Exhaust", Chemical Physics Letters, vol. 28, No. 4, Oct. 15, 1974.

A. C. Metaxas et al. Industrial Microwave Heating, Chapt. 4.7.3, "High Frequency Drying", Peter Peregrinus Ltd., London, UK, 1983, pp. 92–94.

Brochure: SafeTNet 210 and SafeTNet 410.

J. Cuthbert et al., "Microwave Spectroscopy: The Design of an Analytical Spectrometer", Journal of Physics E: Scientific Instruments, vol. 5, 1972.

Sordellini et al., "EtO Sterilization: Principles of Process Design", Medical Device and Diagnostic Industry, Dec., 1998.

* cited by examiner

SAFETY SYSTEM

DESCRIPTION

This invention relates in general to a safety system, and more particularly to an accurate and reliable safety system for a gas sterilization facility which prevents a person from opening the chambers in the facility if dangerous levels of gas are present in the chambers.

BACKGROUND OF THE INVENTION

Gas sterilization facilities exist throughout the world. These sterilization facilities are used to sterilize a variety of articles such as medical devices, surgical instruments and other healthcare supplies and equipment. The sterilization process used to sterilize these articles must completely kill or destroy the microorganisms on these articles.

Ethylene oxide sterilization is a widely used, effective method for sterilizing such articles. Ethylene oxide gas is an extremely effective bactericide for metal objects, such as surgical implements, as well as relatively delicate instruments and equipment including synthetics or plastics. Moreover, since ethylene oxide gas is effective at relatively cool temperatures, the ethylene oxide sterilization process does not employ high temperatures which can degrade articles made of certain materials. Ethylene oxide gas also penetrates certain packaging materials and is therefore effective in sterilizing articles in appropriately designed packages. Ethylene oxide sterilization is preformed on a large scale at sterilization facilities having multiple industrial size sterilization chambers and on a smaller scale at facilities, such as hospitals, which typically have one or relatively few, smaller sterilization chambers. During the ethylene oxide sterilization process, the packaged articles to be sterilized are placed in a sterilization chamber, the door of the chamber is closed, sealed and locked and a process is initiated including drawing a vacuum and sometimes injecting steam in the chamber. Ethylene oxide gas is then introduced into the sterilization chamber for a period of time sufficient to sterilize the articles in the sterilization chamber.

During the sterilization process, certain amounts of the ethylene oxide gas are physically absorbed into the articles undergoing sterilization. After the articles are exposed to certain levels of ethylene oxide gas for a period of time, the ethylene oxide gas in the sterilization chamber (which is not absorbed into the articles) is exhausted or flushed from the chamber. However, the ethylene oxide gas which was absorbed by the articles is not immediately removed from the sterilization chamber. The ethylene oxide gas absorbed by the articles is slowly "desorbed" from the articles back into the sterilization chamber. As the ethylene oxide gas is desorbed from the articles into the sterilization chamber, the desorbed ethylene oxide gas may be exhausted or flushed from the sterilization chamber. However, since desorption occurs over an extended period of time and is an irregular uncontrolled process, even after the sterilization chamber has been exhausted or flushed multiple times, the atmosphere in the sterilization chamber will most likely still contain ethylene oxide gas desorbed from the articles, subsequent to the last exhausting or flushing cycle for the chamber. Even though the amount of ethylene oxide gas that is in the articles can be measured, it is difficult to know when and at what rate the ethylene oxide gas will be desorbed from articles into the sterilization chamber. The sterilization chamber thereby includes a vent exhaust system which is automatically triggered when the door of the chamber is slightly opened. The vent exhaust system directs the vented gas from the chamber to emission control equipment which may include one or more ignition sources.

Ethylene oxide gas is toxic to human beings, flammable and potentially explosive. If the door of a sterilization chamber is opened when a certain level of ethylene oxide gas is present in the chamber (i) due to incomplete exhausting or flushing of the chamber, (ii) after additional ethylene oxide gas is released into the sterilization chamber due to the continued desorption process, (iii) at the wrong time during the sterilization cycle, or (iv) after there has been an unknown equipment or control malfunction, the gas mixture in the vent exhaust system and chamber could be flammable and have the potential to ignite causing an explosion to occur as a result of the explosive gas mixture coming into contact with any of several potential ignition sources. Also, the person opening the chamber or the other people in the sterilization facility could be exposed to the toxic ethylene oxide gas. This creates a potentially dangerous environment for the personnel operating the sterilization facility, especially since the desorption process is irregular and uncontrolled.

For safety purposes, strict procedures must be followed while opening the door to any sterilization chamber. These procedures include creating sufficient vacuum draw downs of the gas in the chamber, followed by a gas in-bleed of air or nitrogen (i.e., gas washes) which removes much of the ethylene oxide gas from the articles and packaging in the chamber. Thereafter, the door of the chamber is slightly opened, which triggers the back vent or vent exhaust system. The back vent draws air into the chamber through the opening between the door and the door frame, to flush out the empty chamber space surrounding the articles and packaging. After a predetermined period, the chamber door may be fully opened to remove the articles and packaging in the sterilization chamber. These procedures may not be followed due to human error, equipment failure or control system failure. Accordingly, there is a need for accurate and reliable safety systems in gas sterilization facilities, and particularly in ethylene oxide sterilization facilities, to measure the level of ethylene oxide gas in the sterilization chamber and to prevent opening of the door to the sterilization chamber if the level of ethylene oxide in the chamber is above a predetermined level.

Microwave spectrometers are generally known for detecting the presence and concentration of ethylene oxide gas and other gases. For example, U.S. Pat. Nos. 5,209,902, 5,399,314 and 5,548,217 disclose the use of microwave spectrometers for detecting the presence and concentration of ethylene oxide gas. Microwave spectrometers have also been employed to measure the concentration of ethylene oxide gas in a sterilization chamber to facilitate parametric release of the articles. For example, Griffith Micro Science, Inc. currently uses microwave spectrometers to facilitate parametric release on a limited number of ethylene oxide sterilization chambers. The microwave spectrometer used by Griffith Micro Science, Inc. is generally described in the publication entitled *Specificity, Accuracy, And Interpretation Of Measurements Of Ethylene Oxide Gas Concentrations During Sterilization Using A Microwave Spectrometer* published in the Rev. Sci. Instrum. (68) 7, July 1997. No known ethylene oxide sterilization facility, however utilizes a microwave spectrometer in a reliable and accurate safety system which prevents access to the sterilization chambers based on the concentration of ethylene oxide gas in the sterilization chambers.

Accordingly, there is a need for an accurate and reliable safety system or other apparatus or method to determine whether it is safe to unlock the door of a sterilization chamber, and in particular an ethylene oxide sterilization chamber, based on the measured concentration of sterilization gas in the sterilization chamber regardless of whether those levels are due to continuing desorption of the sterilization gas from the articles and packaging into the sterilization chamber, human error or equipment or control system malfunction. The desired safety system must prevent the opening of a sterilization chamber when a dangerous level of sterilization gas is present in the sterilization chamber.

SUMMARY OF THE INVENTION

The present invention solves the above problems by providing an accurate and reliable safety system for a gas sterilization facility having one or more sterilization chambers, and in particular, for an ethylene oxide sterilization facility having one or more ethylene oxide sterilization chambers. The safety system of the present invention is adapted to determine if the concentration of ethylene oxide gas in each sterilization chamber is above or below a predetermined level, determines whether it is safe to unlock the door of each sterilization chamber based on the concentration of ethylene oxide gas in the sterilization chamber, limits access to the sterilization chambers if dangerous levels of ethylene oxide gas are present in the sterilization due to the possible continued desorption of the ethylene oxide gas from the articles into the sterilization chambers, and limits the possible effects of human error or equipment or control system malfunction. The present invention thereby improves the overall safety at ethylene oxide sterilization facilities. A sterilization facility having one or more sterilization chambers may have a separate safety system associated with each sterilization chamber, or more preferably, will have a single safety system associated with all of the sterilization chambers in a sterilization facility or a section of the sterilization facility. The safety system will preferably have a dedicated gas measuring apparatus or microwave spectrometer connected to all of the sterilization chambers. The dedicated microwave spectrometer will not be used for facilitating parametric release of the articles. It will be appreciated that the safety system of the present invention could be employed in alternative gas sterilization systems and could be employed in the other types of gas process systems or facilities to measure dangerous levels of specified gases and to limit access to areas based upon such measurements.

The safety system of the present invention generally includes a central processing unit, a master control panel, a chamber control panel on each sterilization chamber, an electropneumatically activated locking mechanism for the door of each sterilization chamber, a gas measuring apparatus such as a microwave spectrometer, a chamber sample valve for each sterilization chamber and a pump connected to the chamber sample valves and the gas measuring apparatus. An operator in the sterilization facility operates the safety system of the present invention through the master control panel or the chamber control panels. The central processing unit controls the operation of the safety system, including the door locking mechanisms, the control panels, the chamber sample valves, the pump and the gas measuring apparatus. The central processing unit may also communicate using electric lines to the computer control system of the sterilization facility. The locking mechanism on the door of each sterilization chamber is adapted to lock and unlock the door upon commands from the central processing unit. The pump and the chamber sample valves are adapted to obtain gas samples from the sterilization chambers upon commands from the central processing unit. The gas measuring apparatus is adapted to determine the presence and the concentration of a specified gas in the gas samples obtained from the sterilization chambers. Gas communication lines or pipes connect the chamber sample valves, the pump and the gas measuring apparatus.

The safety system of the present invention prevents an accidental or inadvertent opening of the doors of the sterilization chambers. After a door of a sterilization chamber is closed and the sterilization cycle begins, the door is locked and the safety system prevents the door from being unlocked until the safety system samples the atmosphere in the sterilization chamber and determines that it is safe for the door to be opened. To unlock the door, an operator in the sterilization facility directs the central processing unit through the master control panel or the chamber control panel of a sterilization chamber to determine if the concentration of ethylene oxide gas in the specified sterilization chamber is above or below a predetermined level. The central processing unit sends a signal to the chamber sample valve of the sterilization chamber to obtain one or more gas samples from the sterilization chamber. The gas samples are directed through the connecting tubes and pump to the gas measuring apparatus. The gas measuring apparatus determines if the concentration of ethylene oxide gas in the gas samples is above a predetermined level. This sampling and measurement process is preferably repeated multiple times to obtain reliable measurements. The gas measuring apparatus sends a signal to the central processing unit as to whether the level of ethylene oxide gas in the gas samples taken from the sterilization chamber is safe or unsafe.

If the level of ethylene oxide gas in the sterilization chamber is unsafe or above a predetermined level, the central processing unit will not unlock the door and will provide a message to the operator via the master control panel and the chamber control panel indicating that there is an unsafe level of ethylene oxide gas in the sterilization chamber. The sterilization chamber may then be further exhausted or flushed. An additional period of time may be required to allow for further flushing of the desorbed ethylene oxide gas. The sampling and measurement process preformed by the safety system will need to be repeated before the door is opened.

If the level of ethylene oxide gas in the sterilization chamber is safe or below a predetermined level, the central processing unit will send a signal to the locking mechanism of the sterilization chamber to unlock the door of the sterilization chamber. The central processing unit will also provide a message to the operator via the chamber control panel and the master control panel that the door is unlocked. The door of the sterilization chamber may then be opened to provide access to the sterilization chamber and to remove the articles which have undergone sterilization.

After the initial measurement is made, the level of ethylene oxide gas in the sterilization chamber could increase to dangerous levels due to the continued desorption of the ethylene oxide gas from the articles in the chamber which may occur at uneven rates. To avoid such potential problems, if the door of the sterilization chamber is not opened after a predetermined period of time, the central processing unit will send a signal to the locking mechanism to re-lock the door of the sterilization chamber, thereby preventing access to the sterilization chamber until further safe measurements are made. The central processing unit will also send a message to the chamber control panel and the master control panels that the door is locked.

The safety system of the present invention employs a microwave spectrometer to reliably and accurately measure the concentration of ethylene oxide gas in the gas samples taken from the sterilization chambers. The microwave spectrometer of the present invention is suitably calibrated to accurately and reliably measure relatively low concentrations of ethylene oxide gas in gas samples. The microwave spectrometer is therefore preferably employed in the safety system, although it should be appreciated that alternative gas measuring apparatus such as infrared, near infra-red, gas chromatographs or other accurate and reliable measuring apparatus could be employed in the safety system of the present invention if they are adjusted or calibrated to accurately and reliably measure such relatively low concentrations of ethylene oxide gas in the sterilization chambers. The safety system of the present invention preferably includes a single dedicated microwave spectrometer for multiple sterilization chambers in a sterilization plant or facility. The gas samples taken from each sterilization chamber are directed to the single microwave spectrometer. One or more back-up microwave spectrometers could also be employed in the safety system of the present invention to enable the safety system to continue to operate if the primary microwave spectrometer malfunctions. A single microwave spectrometer could be connected to each sterilization chamber; however, the use of multiple microwave spectrometers would dramatically increase the cost of the safety system, unnecessarily complicate the safety system and increase the possibilities for malfunction of the safety system.

It is therefore an object of the present invention to provide a safety system for a sterilization facility.

Another object of the present invention is to provide a safety system for a gas sterilization facility having one or more sterilization chambers.

Another object of the present invention is to provide a safety system for a gas sterilization facility which determines if the concentration of sterilization gas in gas samples obtained from a sterilization chamber is above a predetermined level, and prevents access to the sterilization chamber if the level of sterilization gas in the sterilization chamber is unsafe.

A further object of the present invention is to provide a safety system for a sterilization facility which limits access to a plurality of sterilization chambers and minimizes serious consequences as a result of human error or equipment or control system malfunction.

A yet further object of the present invention is to provide a safety system which unlocks the door of the sterilization chamber if the level of sterilization gas in the sterilization chamber is below a predetermined level.

A still further object of the present invention is to provide a safety system for a sterilization facility which determined the concentration of a specified gas in one or more gas samples taken from a sterilization chamber to ensure a reliable measurement.

A yet further object of the present invention is to provide a safety system for a sterilization facility which unlocks the door of a sterilization chamber if the level of sterilization gas in the sterilization chamber is below a predetermined level and relocks the door if the door is not opened after a predetermined period of time.

Other objects, features and advantages of the present invention will be apparent from the following detailed disclosure in conjunction with the accompanying sheets of drawings, wherein like reference numerals refer to like parts.

DETAILED DESCRIPTION OF THE PREFERRED EMBODIMENT

The safety system of the present invention may be used in gas sterilization facilities, and in particular in ethylene oxide sterilization facilities, which include one or more sterilization chambers. The entire ethylene oxide sterilization process including the sterilization chambers is controlled and monitored by an existing sterilization computer control system. The safety system of the present invention will send and receive signals to the various components of the sterilization chamber and may communicate with or may be integrated with this existing computer control system to obtain information from the computer control system and to provide an overall safer sterilization process. It should be appreciated that while the safety system of the present invention is described below in regard to ethylene oxide sterilization facilities, the safety system of the present invention could be used in other gas sterilization processes specifically including but not limited to propylene oxide gas sterilization facilities. Moreover, the safety system could be used in other types of gas process systems or facilities to measure the level of specified gases in chamber and areas and to limit access to such areas based on the measurements.

Figure 1:
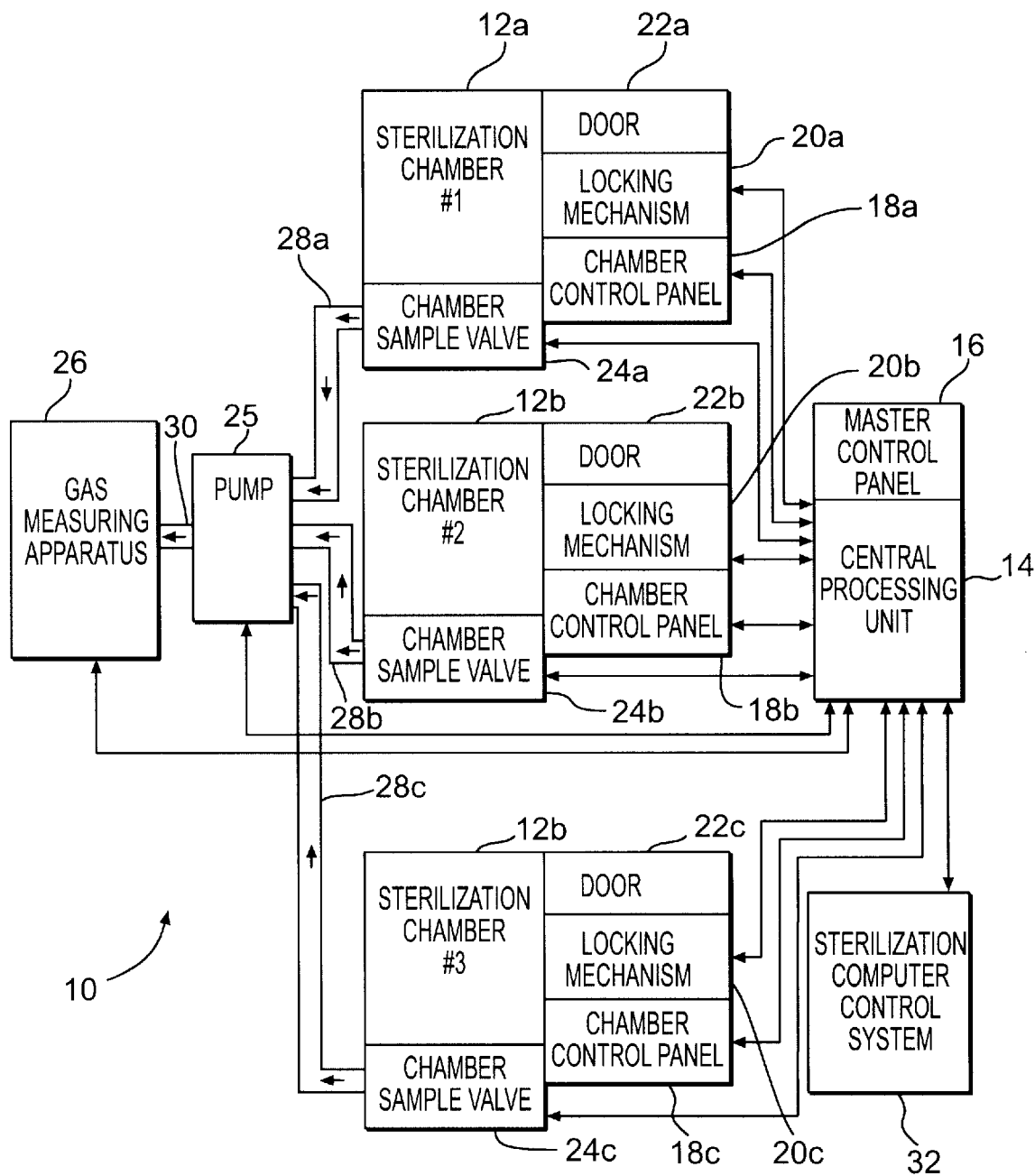
FIG. 1 is a schematic diagram of the safety system of the present invention.

Referring now to the drawings and particularly to FIG. 1, the safety system of the present invention, generally indicated by numeral 10, is adapted for a gas facility having a plurality of gas chambers. For purposes of this application, the safety system of the present invention is described in relation to three gas sterilization chambers, 12a, 12b and 12c. However, the safety system of the present invention could be used for one or two gas sterilization chambers such as in a hospital, for more than three gas sterilization chambers such as in an industrial sterilization facility or for other gas systems or facilities having one or more gas chambers or areas. Sterilization chambers 12a, 12b and 12c are respectively labeled "Sterilization Chamber #1," "Sterilization Chamber #2" and "Sterilization Chamber #3". Each sterilization chamber operates independently of the other sterilization chambers and the safety system of the present invention is adapted to prevent access to each sterilization chamber independent of access to the other sterilization chambers. Specifically, the gas samples obtained from each sterilization chamber must be independently tested before access to that chamber is permitted.

The safety system 10 includes a central processing unit 14, a master control panel 16, chamber control panels 18a, 18b and 18c for the sterilization chambers 12a, 12b and 12c, respectively, locking mechanisms 20a, 20b and 20c for the doors 22a, 22b and 22c of the sterilization chambers 12a, 12b and 12c, respectively, chamber sample valves 24a, 24b and 24c a, 24b and 24c for the sterilization chambers 12a, 12b and 12c, respectively, a pump 25 and a gas measuring apparatus 26. Suitable gas pipes or lines 28a, 28b and 28c connect the chamber sample valves 24a, 24b and 24c, respectively, to the pump 25, and a suitable gas pipe or line 30 connects the pump 25 to the gas measuring apparatus 26. The gas pipes or lines 28a, 28b, 28c and 30 are preferably made of a stainless steel tubing having a relatively small (½ inch) diameter. The lines could be made of other suitable materials, could be alternatively sized and could be insulated.

Generally, the central processing unit ("CPU") 14 is a conventional computer processor adapted and programmed to control the operation of the safety system. As illustrated in FIG. 1, the CPU 14 communicates over a plurality of electric lines with the master control panel 16, the chamber control panels 18a, 18b and 18c, the locking mechanisms 20a, 20b and 20c, the chamber sample valves 24a, 24b and 24c, the pump 25 and the gas measuring apparatus 26. If desired, the CPU 14 may also interface or be connected via electric lines to the sterilization computer control system 32 which controls and monitors the entire sterilization process in the sterilization facility including each of the sterilization chambers. Such gas chamber computer control systems are currently in place in such facilities to control the gas treatment process.

The master control panel 16 which may be attached to the CPU 14 preferably includes a display panel or monitor for indicating the status of the safety system 10 and a keyboard or other suitable input device which enables the operator to give instructions to the CPU 14. The sterilization computer control system 32 which includes an operator workstation, may also be connected to the master control panel 16 so that the master control panel 16 may indicate the status of the sterilization process in each of the sterilization chambers 12a, 12b and 12c as well as the overall status of the safety system. The master control panel allows the operator to determine the status of each sterilization chamber and to test the atmosphere in each sterilization chamber. The operator workstation for the sterilization facility and the master controller may alternatively be combined in a single unit. It should be appreciated that the CPU 14 of the safety system of the present invention could be a separate unit, or alternatively be built into the computer processor in the gas measuring apparatus (i.e., the microwave spectrometer) or the computer processor of the sterilization computer control system.

Figure 2:
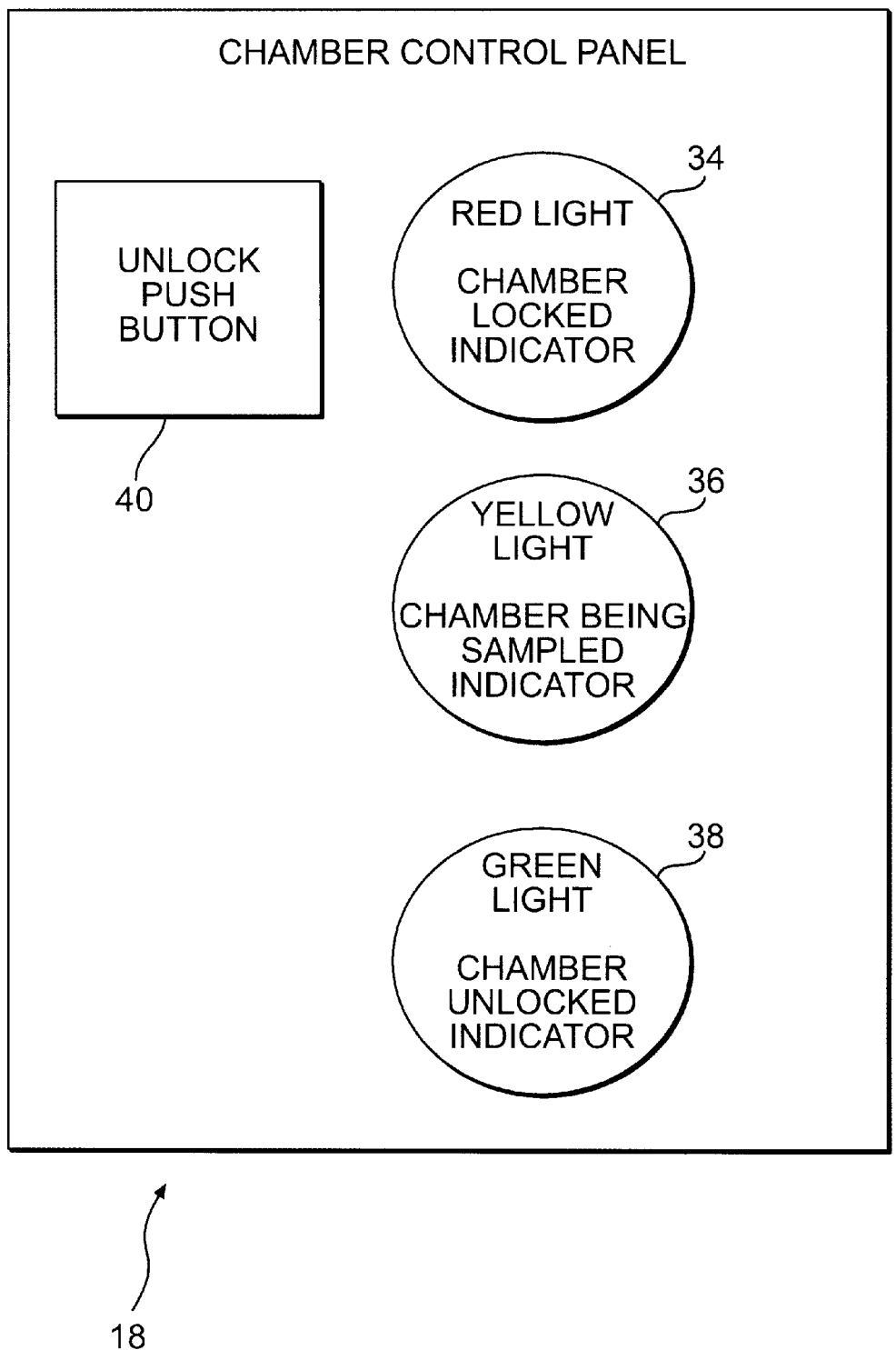
FIG. 2 is a schematic diagram of the chamber control panel of the safety system of the present invention.

The chamber control panels 18a, 18b and 18c are attached to the exterior of the sterilization chambers 12a, 12b and 12c, respectively. As generally illustrated in FIG. 2, each chamber control panel 18 includes a light 34 for indicating that the door of the sterilization chamber is locked, a light 36 for indicating that the safety system is testing gas samples taken from the sterilization chamber to determine the concentration of the ethylene oxide gas inside the sterilization chamber, and a light 38 for indicating that the door locks on the sterilization chamber are open preferably, light 34 is red, light 36 is yellow and light 38 is green. The red chamber locked indicator light 34 will flash if there is a malfunction or problem with the safety system. For instance, the light 34 will flash if the pump 25, the gas measuring apparatus 26 or the chamber sample valves 24a, 24b or 24c fail. The yellow chamber being sampled indicator light 36 will flash if the safety system is waiting for the gas measuring apparatus to finish testing gas samples taken from another sterilization chamber. The green chamber unlocked indicator light 38 will flash when the atmosphere inside the sterilization chamber has been measured and determined to be safe, the door has been unlocked, and the safety system 10 is waiting for the operator to open the door. Additional synchronous lights or indicators may be placed on the top of or in other prominent locations on the sterilization chambers so that the status of the sterilization chambers can be easily observed. The master control panel 16 will preferably include such lights or indicators for each chamber. The chamber control process also includes an "Unlock" push button or switch 40 which an operator may push or activate to direct the safety system 10 to test the atmosphere in the sterilization chamber, and if the atmosphere is safe, to unlock the door of the sterilization chamber. Based on the timer, if the CPU 14 determines that a sufficient period of time has lapsed without the door to a chamber being opened after the testing, the CPU 14 re-locks the door. The operator will then need to push this button 40 to direct the safety system to resample the atmosphere inside the chamber and unlock the door if the atmosphere inside the sterilization chamber is still safe.

Modern sterilization chambers include doors and automatic locking mechanisms which are already controlled by the sterilization computer control system 32. The locking mechanisms are activated by solenoids or other suitable devices. The doors are locked or unlocked by an operator (pushing a button) at the operator station of the sterilization facility. Older sterilization chambers include doors with manual closing mechanisms. Automatic pneumatic locking mechanisms such as those commercially available from Vacudyne Incorporated of Chicago Heights, Ill., have been installed on such older sterilization chambers. These locking mechanisms are also locked or unlocked by an operator (pushing a button) at the operator station of the sterilization facility. The safety system 10 of the present invention utilizes these locking mechanisms on the doors of the sterilization chambers to lock and unlock the doors upon commands from the CPU 14. The safety system 10 thereby controls the locking and unlocking of the doors instead of the existing sterilization computer control system 32. Alternatively, the safety system 10 could allow the sterilization computer control system to continue to lock the doors and only control the unlocking of the doors.

The chamber sample valves 24a, 24b and 24c which are respectively connected to the sterilization chambers 12a, 12b and 12c are adapted to obtain gas samples from inside the sterilization chambers upon commands from the CPU 14. Specifically, each chamber sample valve is preferably a conventional pneumatically actuated solenoid activated valve suitably connected to an existing chamber penetration or port in the wall of the sterilization chamber. The chamber sample valves 24a, 24b and 24c may be connected by gas pipes or lines 28a, 28b and 28c to the pump 25 as illustrated in FIG. 1. The pump 25 is connected to gas measuring apparatus 26 by gas line 30. The pump 25 could continuously exhaust to atmosphere if the concentration of the sterilization gas is low or to a catalytic converter for higher concentrations. The chamber sample valves 24a, 24b and 24c, the pump 25 and the gas measuring apparatus 26 could alternatively be connected in a recirculation loop. As further described below, the chamber sample valve of a sterilization chamber may not be opened if the ethylene oxide sterilization process is occurring in that chamber. The chamber sample valves also will not open unless the pump is running. Only one chamber sample valve may be opened at a time to ensure that the gas measuring apparatus individually measures the gas samples obtained from each sterilization chamber.

The gas measuring apparatus 26 of the safety system 10 measures the concentration of a specified gas in gas samples obtained from the sterilization chambers upon commands from the CPU 14. The gas measuring apparatus 26 of the safety system of the present invention preferably includes a microwave spectrometer for accurately and reliably measuring the concentration of ethylene oxide gas in the gas samples obtained from the sterilization chambers. The microwave spectrometer in the safety system preferably runs continuously. The microwave spectrometer which is described in more detail below is generally disclosed in *Specificity, Accuracy, And Interpretation Of Measurements Of Ethylene Oxide Gas Concentrations During Sterilization Using A Microwave Spectrometer* published in the Rev. Sci. Instrum. (68) 7, July 1997 which is incorporated herein by reference.

Figure 3:
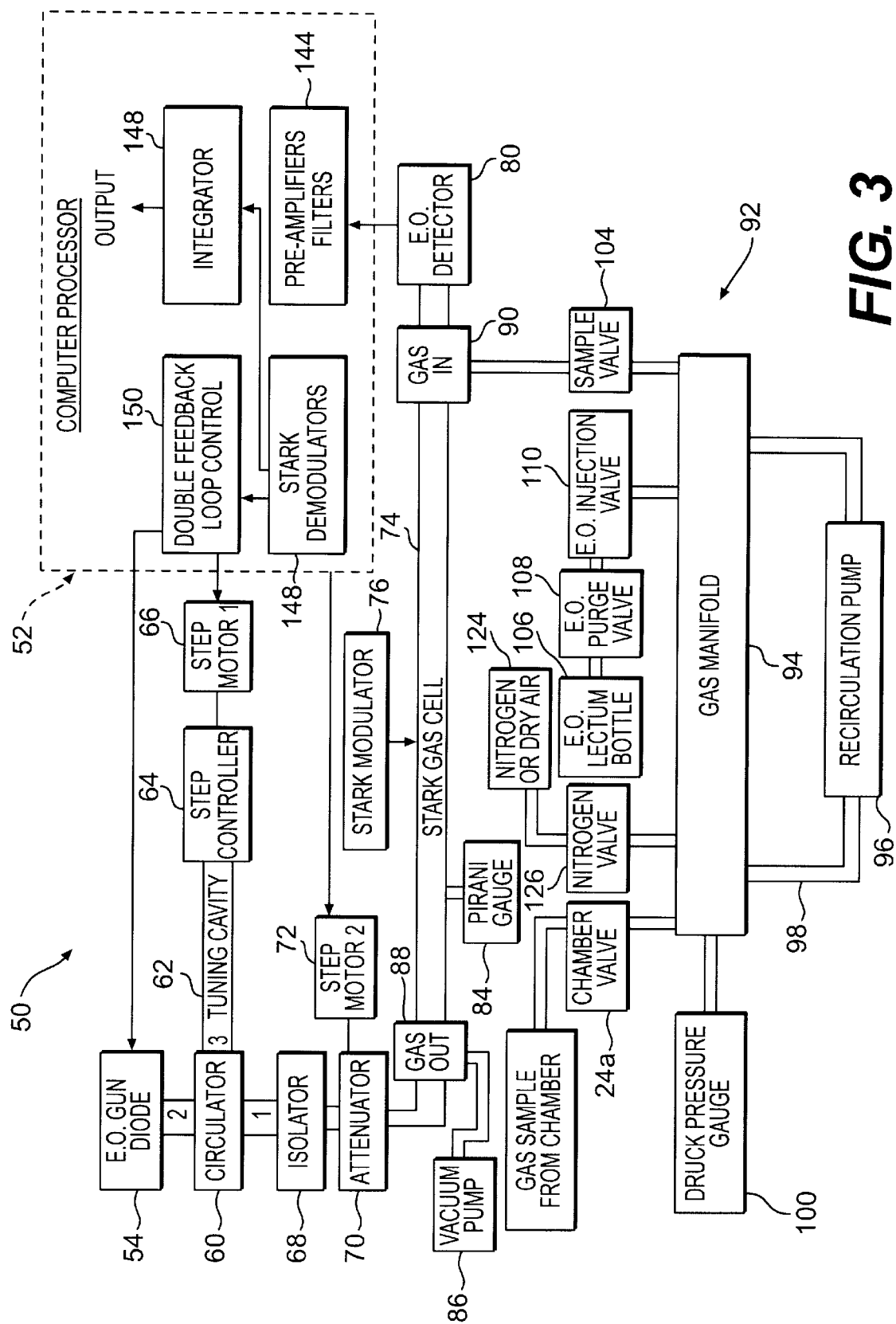
FIG. 3 is a schematic diagram of the gas measuring apparatus or microwave spectrometer of the present invention.
Figure 4:
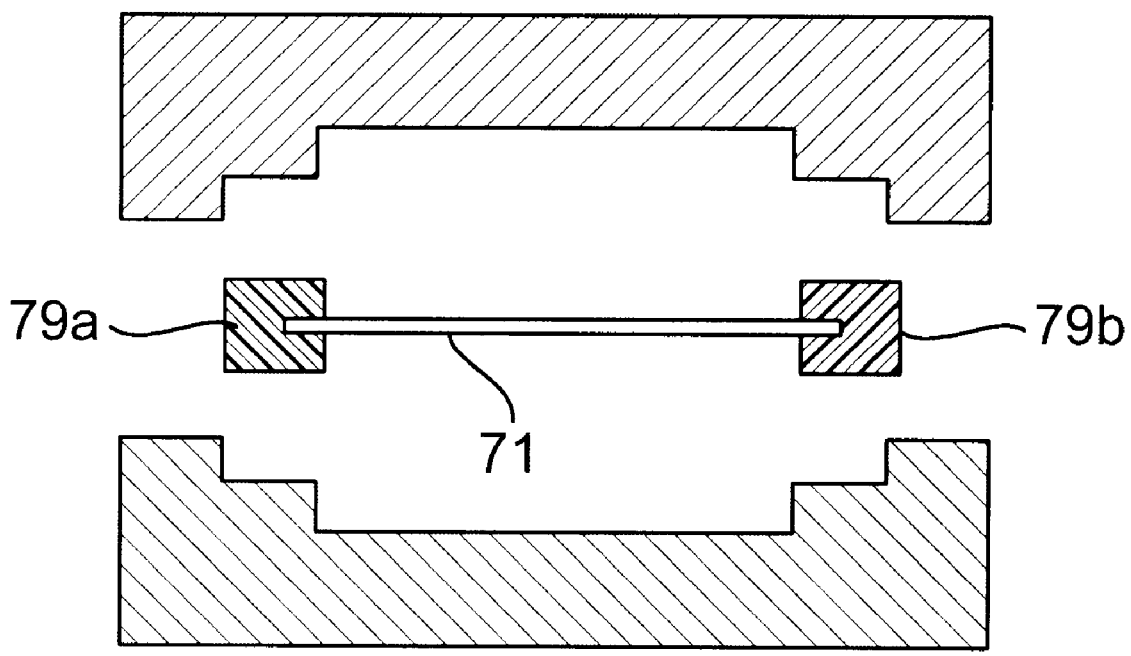
FIG. 4 is an enlarged schematic cross-sectional view of the gas measurement cell and Stark modulator therein.

More specifically, referring now to FIGS. 3 and 4, the microwave spectrometer 50 measures the concentration of ethylene oxide gas in one or more gas samples or sample atmospheres taken from an ethylene oxide sterilization chamber. The microwave spectrometer could alternatively measure the concentration of one or more specified gases in one or more gas samples or sample atmospheres taken from another source.

According to the principles of quantum physics, a gas molecule will absorb the energy or power of microwaves having a specific frequency. Different gas molecules will absorb the energy or power of microwaves at different specific frequencies. The frequency at which a gas molecule will absorb microwave radiation is called the "absorption frequency". The exact absorption frequencies for a large number of gas molecules have been determined and were published in 1968 by the United States National Bureau of Standards. The absorption frequency for an ethylene oxide gas molecule employed in the ethylene oxide sterilization process is 23.134 gigahertz. To measure the concentration of the ethylene oxide molecules in gas samples or sample atmospheres taken from an ethylene oxide sterilization chamber, the improved spectrometer generates microwaves at the absorption frequencies of such molecules, as described below.

The microwave spectrometer 50 is generally constructed or assembled from commercially available components. The microwave spectrometer is controlled by conventional computer and printed circuit board control system 52, which will jointly be referred to herein as the control system 52. The control system 52 includes a plurality of printed circuit boards and computer processor which performs the various functions described below. The microwave spectrometer 50 includes a microwave generator or gun diode oscillator 54 which generate microwaves approximately at the absorption frequency of the ethylene oxide gas molecules. In particular, gun diode 54, which may include a built-in varactor for electronically tuning the frequency, generates microwaves having a small distribution of frequencies about the absorption frequency for the ethylene oxide molecule. The microwaves generated by the gun diode 54 are collected and directed by a circulator 60 to a tuning cavity 62. The circulator 60 directs the microwaves into and out of the tuning cavity 62 and specifically from port 2 to port 3 to port 1.

The tuning cavity 62 refines or modulates the microwave frequencies generated by the gun diode 54 to the exact absorption frequencies of the ethylene oxide molecule. The tuning cavity 62, preferably consists of an empty metal rectangular section of tube although it could be made of other suitable materials, shapes and sizes. By changing the length of the tube, the microwaves are precisely tuned by their travel in the tube to the absorption frequency of the specific ethylene oxide molecule. Specifically, the frequencies of the microwaves are precisely tuned by the distance the microwaves travel in the tube, and by the distance the microwaves that are reflected off the far end wall of the tube travel back in the tube to the circulator 60. The length of the tuning cavity 62 is changed to the exact length necessary to create the appropriate resonant frequency by altering the position (by fractions of millimeters) of the far end wall of the tube which is opposite the circulator 60. The position of the far end wall is altered by a step controller 64 or tunable short circuit attached to the tube which is driven by an electric step motor 66. Based on commands from the control system 52, the step motor 66 drives the step controller 64 to adjust the position of the far end wall and thereby the length of the tube. Accordingly, the tuning cavity must have extremely tight tolerances and must strictly comply with desired manufacturing specifications.

After the microwaves are precisely tuned by the tuning cavity 62, they are channeled back through the circulator 60 to an isolator 68. The circulator 60 channels the precisely tuned microwaves so that they do not re-enter the tuning cavity 62. The isolator 68 prevents the microwaves from being reflected back to the circulator 60 or the tuning cavity 62. The isolator 68 also channels the microwaves to an attenuator 70. The attenuator 70 modulates (i.e., reduces) the amplitude of the microwaves as necessary based on commands from the control system 52 to obtain the desired power or energy level for the microwaves (i.e., so that the microwave signal is constant.) The attenuator 70 is controlled by a second step motor 72 which adjusts the power level. The step motor 72 is controlled by the control system 52. The attenuator directs the microwaves to a gas measurement cell 74, and in particular through a microwave input port in one end of the gas measurement cell 74. The control system 52 thereby determines, regulates and knows the amplitude, power or energy level of the microwaves before the microwaves enter the gas measurement cell 74.

The gas measurement cell 74 is also referred to as a Stark gas cell because it includes a Stark modulator 76 of the kind well known in the field. The Stark modulator 76, the structure of which is generally illustrated in FIG. 4, includes a standard steel electrode 71 mounted on teflon insulators 79a and 79b. The microwaves, which are modulated by the Stark modulator 76 travel through the gas measurement cell 74 and exit the gas measurement cell 74 through a microwave output port at the opposite end of the gas measurement cell 74. The gas measurement cell 74 is preferably a fifty centimeter commercially available waveguide tube of suitable materials, shapes and sizes. The modulated microwaves having a specific frequency travel through the gas measurement cell 74 and will interact with any gas molecules in the gas measurement cell 74 having an absorption frequency equal to the specific frequency of the microwaves, as described below. The microwaves will not interact with any gas molecules in the gas measurement cell 74 having a different absorption frequency. Therefore, the microwave spectrometer accurately and reliably measures only the ethylene oxide or other sterilization gas present in the gas samples.

A solid state tunable ethylene oxide microwave detector 80 is connected to a microwave output port of the gas measurement cell 74. The detector 80 detects the amplitude, power or energy of the microwaves having a frequency approximately equal to the ethylene oxide absorption frequency after the microwaves have traveled through the gas measurement cell 74. The detector 80 sends the measurements it makes to the control system 52. The control system 52 determines the concentration of the ethylene oxide by determining the amount of power absorbed by the molecules in the gas measurement cell 74 based on the difference in the power or energy of the microwaves regulated by the attenuator 70 and the power or energy of the microwaves measured by detector 80.

A Pirani pressure gauge or transducer 84 measures the pressure in the gas measurement cell 74. The pressure in the gas cell 74 is preferably maintained at a relatively low pressure and particularly at about 1/10 of a millibar to prevent the ethylene oxide molecules from frequently bumping into each other based on rotational energy levels which may disrupt the microwave absorption process. The pirani pressure gauge 84 sends a signal to the control system 52 indicating the pressure in the gas measurement cell 74. The control system 52 will measure the pressure in the gas measurement cell 74 and is used for the concentration determination. The vacuum pump 86 is connected to a gas output port 88 in the gas measurement cell 74. The vacuum pump 86 is adapted to draw gas samples into the gas measurement cell 74 through a gas input port 90. The gas input port 90 in the gas measurement cell 74 is connected to a calibration/sampling and dilution gas system 92. The vacuum pump 86 may continuously draw on or may draw at desired intervals gas samples into the gas measurement cell 74. Single or multiple measurements are made in the gas measurement cell 74. The vacuum pump 86 then exhausts the gas samples from the gas measurement cell 74.

The calibration/sampling and dilution gas system 92, which is also herein referred to as the gas sampling system 92, includes a gas manifold 94 which collects the gas samples before they are communicated to the gas measurement cell 74. A recirculation pump 96 and recirculation loop 98 are suitably connected to the gas manifold 94 to draw gas samples into and to mix the gas samples in the gas manifold 94. A Druck pressure gauge 100 is also connected to the gas manifold 94 for measuring the pressure in the gas manifold 94. When it is desired to take a measurement, the CPU 14 opens the chamber sample valve 24a. The chamber sample valve 24a opens to allow a gas sample from the ethylene oxide sterilization chamber into the gas manifold 94 via the pump 25 (see FIG. 1). When a gas sample is taken from the sterilization chamber 12a and the chamber sample valve 24a is opened, the gas sample is drawn into the gas manifold 94 by the recirculation pump 96. The gas sampling system 92 includes a sample valve 104 connected to the gas manifold 94 and the gas input port 94 of the gas measurement cell 74. The control system 52 signals the sample valve 104 to open allowing the gas sample collected in the gas manifold 94 to be drawn into the gas measurement cell 74 to facilitate the microwave spectrometer's measurement of the gas sample. The gas sampling system 92 is thereby suitably connected to the ethylene oxide sterilization chamber and facilitates obtaining one or more gas samples from the sterilization chamber for the microwave spectrometer 52 to measure.

The gas sampling system 92 also obtains a second gas sample for calibrating the microwave spectrometer for measuring the concentration of ethylene oxide gas. The gas sampling system 92 includes an ethylene oxide lecture bottle 106 containing pure ethylene oxide. The lecture bottle 106 is connected to the gas manifold 94 through an ethylene oxide purge valve 108 and an ethylene oxide injector valve 110. When the computer control system 52 calibrates the microwave spectrometer 50 to measure ethylene oxide gas, the computer control system 52 sends signals to the ethylene oxide purge valve 108, the ethylene oxide injector valve 110 and the nitrogen valve 126 (described below) which co-act to inject ethylene oxide vapor and nitrogen into the gas manifold 94. Actual known concentrations of ethylene oxide gas are thereby prepared and input into the gas measurement cell 74 to calibrate the microwave spectrometer for measuring the concentration of ethylene oxide gas.

The gas sample obtained from the sterilization chamber and the lecture bottle 106 are preferably diluted in the gas manifold 94 before they are drawn into the gas measurement cell 74. For this purpose, a suitable source 124 of nitrogen, dry air or other suitable gas is connected to the gas manifold 94 through a nitrogen valve 126. Subsequent to obtaining such gas samples in the gas manifold and before allowing a gas sample to enter the gas measurement cell 74, the control system 52 sends a signal to the nitrogen valve 126 which opens to allow nitrogen gas (or another suitable gas) into the gas manifold 94.

The principal of calibration is in part based on the ideal gas law which provides that in a gas mixture, the sum of the partial pressures of the constituents of that gas mixture equals the total pressure of the system. The concentration of any individual constituent of the mixture can be expressed as the partial pressure divided by the total pressure. Since a certain amount of water vapor is present in the gas samples taken from the ethylene oxide sterilization chamber which is operated approximately at forty to fifty degrees centigrade. The gas sample is preferably diluted with nitrogen gas or another suitable gas by a factor of five, which reduces that the number of molecules in the sample atmosphere to obtain better measurements. The dilution provides an ancillary benefit, in terms of calibration, that when there are fewer molecules to be measured, the width of that microwave absorption peak, is narrower. More detailed information regarding the gas dilution of the sample atmospheres is well known and described in an article entitled *Quantitative Measurement of Analyte Gases in a Microwave Spectrometer Using Dynamic Sampling Method* published in Rev. Sci. Instrum., Vol. 67, No. 7, July 1996, which is incorporated herein by reference.

The control system 52 of microwave spectrometer 50 is connected to gun diode 54, circulator 60, step motors 64 and 72, detector 80, gauges 84 and 100, pumps 86 and 96, and valves 104, 106, 108, 110, and 126 to control, regulate and obtain information necessary for the operation of the microwave spectrometer 50. The control system 52 includes a conventional computer processor, pre-amplifier filters 144 for filtering the signal obtained from the detector 80, one or more stark demodulators 146 for demodulating the signal, an integrator 148 for signal conditioning or tuning, and a double feedback loop control 150 for sending signals to the gun diode 54 and the step motor 66 for modifying or tuning the frequency of the microwaves.

The microwave spectrometer 50 preferably will first calibrate itself for measuring ethylene oxide gas. To calibrate itself for ethylene oxide gas measurements, the gas manifold 94 is cleaned and a diluted gas sample having a known concentration of ethylene gas molecules is obtained in the gas manifold 94. The gun diode 54 generates microwaves which are directed through circulator 60 to the tuning cavity 62. The microwaves are tuned in the tuning cavity and redirected through the circulator 60 into the isolator 68 and then to the attenuator 70 which modulates the amplitude of the microwaves. The microwaves are directed into the gas measurement cell 74 where they are subjected to Stark modulation.

The gas sample in the gas manifold 94 having a known concentration of ethylene oxide gas is channeled from the gas manifold 94 to the gas measurement cell 74 where the microwaves interact with the gas sample. The ethylene oxide molecules absorb the energy of the microwaves having a frequency equal to the absorption frequency of the ethylene oxide molecules. The microwaves are directed to the detector 80 which measures the amplitude of the microwaves. The detector 80 sends this measurement to the control system which determines how much power was absorbed by the ethylene oxide gas in the gas sample as the microwaves traveled through the gas measurement cell 74. After the measurement is taken, the gas sample is exhausted from the gas measurement cell 74.

If the amount of power detected is less than the amount of power which enters the gas measurement cell 74, the control system 52 determines the absorbed power and the concentration of ethylene oxide gas in the gas sample in the gas measurement cell 74. During the calibration adjustment procedure, since the concentration of the ethylene oxide gas is known, the control system determines if the concentration of ethylene oxide it determined is accurate. If the measurement is accurate, the control system knows that it is accurately measuring the concentration of ethylene oxide in the gas sample and no adjustment is made. If the measurement is inaccurate, the control system makes an offset adjustment to match the calibration curve.

After the appropriate calibration adjustment, the microwave spectrometer is ready to take measurements of the gas samples obtained from the sterilization chamber. The gas manifold 94 is cleaned and a diluted gas sample is obtained from the sterilization chamber. The microwave spectrometer may first measure the concentration of the ethylene oxide gas in the gas sample. Similar to the ethylene oxide calibration procedure, the gun diode 54 generates microwaves which are directed through circulator 60 to the tuning cavity 62. The microwaves are tuned in the tuning cavity and redirected through the circulator 60 into the isolator 68 and then to the attenuator 70 which modulates the amplitude of the microwaves. The microwaves are directed into the gas measurement cell 74 where they are subject to Stark modulation. The gas sample in the gas manifold 94 having an unknown concentration of ethylene oxide gas is channeled from the gas manifold 94 to the gas measurement cell 74 where the microwaves interact with the gas sample. The ethylene oxide gas in the gas sample absorbs the energy of the microwaves having a frequency equal to the absorption frequency of the ethylene oxide molecules. The microwaves are directed to the detector 80 which measures the amplitude of the microwaves. The detector 80 sends this measurement to the control system which determines how much power was absorbed by the ethylene oxide gas in the gas sample as the microwaves traveled through the gas measurement cell 74. The microwave spectrometer thereby determines the concentration of the ethylene oxide gas in the gas sample taken from the sterilization chamber. Multiple measurements may be taken of the concentration of the ethylene oxide gas in the gas sample and several gas samples may be measured.

The improved microwave spectrometer utilizes one or more conventional uninterruptable power supplies which provides uninterrupted power to the computer control system and the entire microwave spectrometer.

The microwave spectrometer could also include additional microwave generators and microwave detectors for measuring the concentration of additional specified gases. The microwave spectrometer will include one or more additional circulators for directing the microwaves generated by the gun diodes to the tuning cavity and one or more additional circulators for directing the microwaves from the gas measurement cell to the appropriate detector. Additionally, for each additional gas measured by the microwave spectrometer, an appropriate calibration system will be included in the gas sampling system. It should therefore be appreciated that the safety system of the present invention could be employed on gas sterilization chamber or in other gas processes for measuring the concentration of more than one specified gases.

Alternative gas measuring apparatus could be employed in the safety system to determine the concentration of gas in the gas samples taken from the sterilization chamber. The safety system of the present invention includes a single microwave spectrometer for multiple sterilization chambers in a sterilization plant or facility. One or more back-up microwave spectrometers or other measuring devices could be employed in the safety system which is connected to one or more sterilization chambers. Alternatively, a single microwave spectrometer could be connected to each sterilization chamber.

After the safety system 10 of the present invention is installed in a sterilization facility and supplied with an appropriate power supply, the CPU 14 is initialized with the appropriate information regarding the sterilization chambers and may establish communication with the sterilization computer control system 32. The safety system then operates in conjunction with the sterilization process. The CPU 14 awaits signals from the master control panel 16, the chamber control panels 18a, 18b or 18c or alternatively the computer control system 32 for each sterilization chamber. The CPU 14 will process signals regarding each sterilization chamber independently from the other sterilization chambers and will only test the gas samples taken from a single sterilization chamber at a time. The safety system is described below in regard to Sterilization Chamber No. 1, however, it should be appreciated that all of the sterilization chambers are tested in the same manner.

Prior to the beginning of a sterilization process, the door 22a of sterilization chamber 12a is open. When the door 22a is open, a conventional door sensor (or limit switch) on the sterilization chamber 12a may send a "Door Open" signal to the computer control system 32 and to the CPU 14. Upon receipt of a "Door Open" signal, the CPU 14 will continue to await further signals pertaining to Sterilization Chamber No. 1 (as well as the sterilization chambers No. 2 and No. 3). Both computer systems thereby know if the door 22a of the sterilization chamber 12a is open or closed. The ethylene oxide sterilization process begins when an operator loads a pallet of articles which will undergo sterilization in sterilization chamber 12a. After loading the articles in the chamber, the operator will close the door 22a to the sterilization chamber 12a. When the door is closed, the door sensor will stop sending a "Door Open" signal to the computer control system 32 and the CPU 14. If the CPU 14 stops receiving the "Door Open" signal from the sterilization chamber 12a, it knows that the door on the sterilization chamber 12a has been closed. Multiple door sensors for each door may be used to ensure the accuracy of the signal.

The operator will then press an appropriate button or give a suitable command to the computer control system 32 via the operator workstation or the workstation combined with master control panel. If the control system 32 is not receiving a "Door Open" signal for that sterilization chamber 12a, the control system 32 will then send a "Lock Door" signal to the locking mechanism 20a on the sterilization chamber 12a to lock the door when the sterilization cycle begins. Upon receipt of the "Lock Door" signal, the locking mechanism 20a will lock the door 22a and thereby prevent anyone in the sterilization facility from opening the door. The CPU 14 will also receive this signal from the locking mechanism 20a or the computer control system 32. If the CPU 14 does not receive a "Lock Door" signal, it will await further signals from the computer control system 32. The computer control system may alternatively send the "Lock Door" signal directly to the CPU 14. When the CPU 14 receives a "Lock Door" signal, the CPU 14 will send the "Lock Door" signal to the locking mechanism 20a on the sterilization chamber 12a.

The CPU 14 or the computer control system 32 sends the "Lock Door" signal to the locking mechanism 20a and preferably receives verification that the chamber door 22a is locked or a "Chamber Locked" signal. If the CPU 14 does not receive this verification it will send an appropriate error message. A pressure switch on the cylinder of the locking mechanism could send the verification signal if desired. The CPU 14 will then send a "Chamber Locked" signal to the chamber control panel 18a and the master control panel 16, and may send this signal to the computer control system 32. A pressure switch on the cylinder of the locking mechanism could send the verification signal if desired. The chamber control panel will indicate that the door of the sterilization chamber is locked by lighting up the red chamber locked indicator light 34. The safety system 10 thereby prevents an accidental or inadvertent opening of the door 22a of the sterilization chamber 12a prior to the determination that it is safe to open the door. The sterilization process cycle starts and the door 22a of the sterilization chamber 12a is locked.

The control system 32 then starts the recirculation blower for the sterilization chamber 12a. The recirculation blower mixes the gas in the sterilization chamber and runs continuously through the sterilization process. The CPU 14 of the safety system always knows when the sterilization process is in progress because the recirculation blower sends a "Cycle In-Process" signal to the computer control system blower is working and that the sterilization process is in progress. While the CPU 14 receives the "Cycle In Process" signal, it will not allow the chamber sample valve 24a to open or the locking mechanism 20a to unlock the door 22a. During the sterilization process, the safety system will thereby keep the door 22a locked and will not allow access to sterilization chamber 12a.

The CPU 14 may run the pump 25 continuously. Alternatively, after the sterilization process is complete and the "Cycle In-Process" signal for sterilization chamber 12a is no longer received from the computer control system 32, the CPU 14 may send a "Run Pump" signal to the pump 25 to start the circulation of gas in line 28a from the chamber sample valve 24a of the sterilization chamber 12a to the gas measuring apparatus 26. In either case, the pump 25 sends a "Pump Running" signal to the CPU 14 which indicates that the pump is running. If the CPU does not receive the "pump running" signal if will send an error message.

After the sterilization process is complete, as indicated by the computer control system either presses the "Unlock" push button on the chamber control panel 18a or gives the appropriate command to the master control panel 16. The chamber control panel 18a or the master control panel 16 sends an "Unlock Chamber Request" signal to the CPU 14. The CPU 14 begins the testing process to determine the concentration of ethylene oxide gas in gas samples taken from the sterilization chamber 12a. The CPU 14 sends a "Chamber Being Sampled" signal to the chamber control panel 18a and the master control panel 16. The chamber control panel 18a indicates that the atmosphere in the sterilization chamber 12a is being tested, by lighting up the yellow chamber being sampled indicator light 36. The red chamber locked indicator light 34 also remains illuminated. If another sterilization chamber is undergoing sampling and measurement, the CPU 14 will wait for the other sampling and measurement of the other chamber to complete and will send a signal to the chamber control panel 18a and master control panel 16 indicating that the safety system is waiting for other testing to be completed. The yellow light will flash indicating the status of the system.

The CPU 14 then sends an "Open Valve" signal to the chamber sample valve 24a to open the chamber sample valve 24a to allow gas samples in the sterilization chamber to enter the gas line 28a and be directed by the pump 25 to the gas measuring apparatus 26. The chamber sample valve and pump 25 thereby co-act to obtain gas samples from the sterilization chamber 12a. The CPU 14 then sends a "Measurement" signal to the gas measuring apparatus 26 to begin the measurement process. The gas sampling apparatus 26 determines the concentration of ethylene oxide gas in the gas samples and determines if the level of ethylene oxide gas in the gas samples is above a predetermined level.

For example, a safe level of ethylene oxide gas is below 3% by volume, although a safety factor of four is typically applied, so the set point may be 0.75% by volume in the sterilization chamber. The gas measuring apparatus 26, which preferably includes a microwave spectrometer, will take multiple measurements of the gas samples obtained from the sterilization chamber 12a at atmospheric pressure. The sample system pumps gas samples continuously and the spectrometer takes multiple measurements. Alternatively, the CPU 14 may cause the chamber sample valve 24a to open a plurality of times to allow a plurality of gas samples into the gas measurement apparatus 26. By taking multiple measurements of multiple gas samples from the sterilization chamber, the gas measurement apparatus may obtain reliable measurements of the concentration of ethylene oxide gas in the sterilization chamber. The gas measuring apparatus bases its determination of whether the level is safe or unsafe on all of the measurements. If any measurement is above the predetermined level, the gas measuring apparatus will determine that the level is unsafe. As mentioned above, the chamber sample valves 24a, 24b and 24c, the pump 25 and the gas measuring apparatus could alternatively be connected in a recirculation loop. The gas samples obtained from the chamber sample valves would be directed in the loop to the gas measuring apparatus.

If the level is above the predetermined level, the gas sampling apparatus 26 will send a "Sample Unsafe" signal to the CPU 14. If the CPU 14 receives a "Sample Unsafe" signal, it will not send an "Unlock Door" signal to the locking mechanism 20a and will continue to send the "Chamber Locked" signal to the chamber control panel 18a on the sterilization chamber 12a. The CPU 14 will send a signal to the master control panel 16 indicating that there is an unsafe level of ethylene oxide gas in the sterilization chamber 12a. The CPU 14 also may send this "Sample Unsafe" signal to the computer control system 32, or an operation will interface with the computer control which will cause further exhausting of the atmosphere in the sterilization chamber 12a. An additional period to allow for further flushing of the ethylene oxide gas may be necessary. The entire sampling and measurement process will need to be repeated before access to the sterilization chamber 12a is allowed by the safety system 10.

If the CPU 14 receives a "Sample Safe" signal from the gas measuring apparatus 26, the CPU 14 will send an "Unlock Door" signal to the locking mechanism 20a. The locking mechanism 20a, upon receipt of the "Unlock Door" signal, will unlock the door 22a on the sterilization chamber 12a. The CPU 14 will also send a "Chamber Unlocked" signal to the chamber control panel 18a to flash the green chamber unlocked indicator light 38. The chamber locked indicator light 34 and the chamber being sampled indicator light 36 will no longer be illuminated. The door 22a of the chamber 12a may then be opened to provide access to the sterilization chamber and to remove the articles which have undergone sterilization. When the door is opened the green light will be consistently illuminated.

After the appropriate gas samples are taken from the sterilization chamber, the CPU 14 will continuously run the pump 25 or may alternatively send a "Stop Pump" signal to the pump 25 if there are no other sterilization chambers waiting to be tested. If another sterilization chamber is waiting to be tested, the pump 25 will exhaust gas in the lines (or the recirculation loop) to ensure that the samples from the sterilization chambers are not mixed.

After the initial measurement is made, the level of ethylene oxide gas in the chamber could increase to dangerous levels because the desorption of the ethylene oxide gas from the articles in the chamber which have undergone sterilization may continue at unpredictable uneven rates. To avoid such potential problems, when the signal to open the door of the sterilization chamber is initiated, the CPU 14 will begin a timer for the sterilization chamber 12a. The timer will preferably be thirty minutes or less. If the door 22a is not opened within this predetermined period of time, the CPU 14 will send a signal to the locking mechanism to re-lock the door 22a, thereby preventing access to the sterilization chamber 12a. After the door is re-locked, to obtain access to the sterilization chamber 12a, the entire sampling and measurement process will need to be repeated. An operator can easily repeat the process by pressing the "Unlock" push button 40.

It will be understood that modifications and variations may be effected without departing from the scope of the novel concepts of the present invention, and it is understood that this application is to be limited only by the scope of the appended claims.

The invention is hereby claimed as follows:

1. A safety system for a gas sterilization facility including at least one sterilization chamber, each said sterilization chamber having a door for accessing the sterilization chamber, said safety system comprising:

a locking mechanism connected to the door of each sterilization chamber;

a gas measuring apparatus adapted to measure the concentration of a specified sterilization gas used in the sterilization chambers to sterilize articles;

a chamber sample valve connected to each sterilization chamber;

gas communication lines connecting each chamber sample valve and the gas measuring apparatus;

a central processing unit; and electric communication lines connecting the central processing unit and each locking mechanism, each chamber sample valve and the gas measuring apparatus;

whereby under the control of the central processing unit, each chamber sample valve selectively opens to obtain one or more gas samples from each sterilization chamber, the gas measuring apparatus determines the concentration of the specified sterilization gas in said gas samples and the locking mechanism unlocks the door of the sterilization chamber if the concentration of the specified sterilization gas in said gas samples obtained from said sterilization chamber is below a predetermined level, the central processing unit including means for measuring the length of time which lapses after the locking mechanism unlocks the door of the sterilization chamber and for relocking the door of the sterilization chamber if the door is not opened within a predetermined time.

2. A safety system for an ethylene oxide sterilization facility including a plurality of sterilization chambers, each said sterilization chamber having a door for accessing the sterilization chamber, said safety system comprising:

a locking mechanism connected to the door of each sterilization chamber;

a chamber sample valve connected to each sterilization chamber;

a microwave spectrometer adapted to measure the concentration of ethylene oxide in a gas sample taken from any of the sterilization chambers;

a pump connected to each chamber sample valve and the microwave spectrometer;

gas communication lines connecting the chamber sample valves, the pump and the microwave spectrometer;

a central processing unit;

a timer adapted to measure the length of time which lapses after the locking mechanism of each sterilization chamber is unlocked; and electric communication lines connecting the central processing unit and each locking mechanism, each chamber sample valve, the microwave spectrometer, the pump and the timer;

whereby under the control of the central processing unit, the chamber sample valves selectively open to obtain one or more gas samples from the sterilization chambers, the pump directs the gas samples in the gas communication lines to the microwave spectrometer, the microwave spectrometer measures the concentration of ethylene oxide gas in said gas samples, if the concentration of the ethylene oxide gas in said samples is below a predetermined level, the locking mechanism unlocks the door of the sterilization chamber, the timer measures the length of time which lapses after the locking mechanism unlocks the door of the sterilization chamber, and if the door is not opened within a predetermined period of time, the locking mechanism relocks the door of the sterilization chamber.

3. The safety system of claim 2, which further includes a chamber control panel for each sterilization chamber, and an electric communication line connecting the central processing unit and each chamber control panel.

4. The safety system of claim 3, wherein the chamber control panel includes an indicator light for indicating that the sterilization chamber is locked, and indicator light for indicating that the atmosphere in the sterilization chamber is being sampled or is awaiting sampling, and an indicator light for indicating that the sterilization chamber is unlocked.

5. The safety system of claim 2, which further includes a master control panel and an electric communication line connecting the central processing unit and the master control panel.

6. A safety system for a gas sterilization facility including at least one sterilization chamber, each said sterilization chamber having a door for accessing the sterilization chamber, said safety system comprising:

means for controlling the safety system;

means connected to each sterilization chamber for sampling the gas in such sterilization chamber upon command from the control means;

means for measuring the concentration of a specified gas in the gas sample taken from each sterilization chamber;

means for directing the gas samples from each sterilization chamber to the gas concentration measuring means;

means for communicating the concentration of the specified gas to the control means;

means on each sterilization chamber for locking and unlocking the door on said sterilization chamber; and means for measuring the length of time which lapses after the locking means of each sterilization chamber is unlocked and for the relocking the locking means of each sterilization chamber if the door is not opened within a predetermined period of time.

7. A safety system for a gas sterilization facility, said sterilization facility including a plurality of sterilization chambers each having a door for accessing the sterilization chamber, said safety system comprising:

means for locking the door of each sterilization chamber;

means for obtaining one or more gas samples from each sterilization chamber;

means for measuring the concentration of a sterilizing gas in said gas samples obtained from the sterilization chambers;

means for unlocking the door of the sterilization chamber if the concentration of said sterilizing gas in the said gas samples obtained from said sterilization chamber is below a predetermined level; and means for re-locking the door of said sterilization chamber after a predetermined period of time if the door of said sterilization chamber is not opened.

8. The safety system of claim 7, wherein the means for measuring the level of sterilizing gas in the sterilizing chamber includes a microwave spectrometer.

9. A method for preventing access to a gas sterilization chamber in a sterilization facility if there are dangerous levels of a specified sterilization gas in the sterilization chamber, said sterilization chamber having a door for accessing the sterilization chamber and a locking mechanism for locking said door, said method comprising the steps of:

locking the door of the sterilization chamber;

completing the sterilization process;

obtaining a gas sample from the sterilization chamber;

transferring said gas sample to a gas measuring apparatus;

determining the concentration of said specified sterilization gas in the gas sample;

determining if the concentration of the specified sterilization gas in the gas sample is above, at or below a predetermined dangerous level;

maintaining the door locked if the level of the specified sterilization gas in the gas sample is at or above the predetermined dangerous level;

unlocking the door if the level of the specified sterilization gas in the gas sample is below the predetermined dangerous level;

measuring the period of time after the door is unlocked; and re-locking the door after a predetermined period of time if the door of the sterilization chamber is not opened to prevent access to the sterilization chamber.

* * * * *